(12) United States Patent
Mizushima

(10) Patent No.: US 6,475,535 B1
(45) Date of Patent: Nov. 5, 2002

(54) HOT FOMENTATIONS

(75) Inventor: Noriyasu Mizushima, Tokyo (JP)

(73) Assignee: Sanpo Chemical Co., Ltd., Tokyo (JP)

(*) Notice: Subject to any disclaimer, the term of this patent is extended or adjusted under 35 U.S.C. 154(b) by 0 days.

(21) Appl. No.: 09/424,264

(22) PCT Filed: May 19, 1998

(86) PCT No.: PCT/JP98/02192

§ 371 (c)(1),
(2), (4) Date: Nov. 19, 1999

(87) PCT Pub. No.: WO99/59509

PCT Pub. Date: Nov. 25, 1999

(51) Int. Cl.[7] .......................... A61K 35/78; A61K 9/70; A61K 33/26; A61K 9/72; A01N 25/34
(52) U.S. Cl. ..................... 424/756; 424/725; 424/402; 424/443; 424/40; 424/646
(58) Field of Search ................................ 424/725, 756, 424/402, 40, 443, 646

(56) References Cited

FOREIGN PATENT DOCUMENTS

| JP | 57-81813 | 10/1955 |
|---|---|---|
| JP | 60-13710 | 1/1985 |
| JP | 61-179149 | 8/1986 |
| JP | 4-208154 | 7/1992 |
| JP | 6-22996 | 2/1994 |

Primary Examiner—Thurman K. Page
Assistant Examiner—Amy Pulliam
(74) Attorney, Agent, or Firm—Armstrong, Westerman & Hattori, LLP

(57) ABSTRACT

A hot-type compress which does not form the skin rashes on the applied region thereof. The hot-type compress is constructed so that an applying face side composed of a sticky poultice plaster body formed on one side of a substrate sheet comprises the sticky poultice plaster body and powder or extract of ginger. A stable and good warmth-feeling stimulation is exerted on the skin without having any bad effect thereon by the ginger extract.

2 Claims, 3 Drawing Sheets

HOT FOMENTATIONS

TECHNICAL FIELD

The present invention relates to a hot-type compress used for applying to the affected part of a human body.

BACKGROUND ART

There has been hitherto known a hot-type compress so constructed that a sticky poultice plaster body prepared by kneading extract of capsicum as a skin stimulating agent with a sticky cold-type poultice as a principal component is coated and formed on one side of a substrate sheet so that the capsicum extract may be contained uniformly in an applying layer of the coat layer of the plaster body. When this hot-type compress is applied to the affected part of a human body, it has been found that a warmth-feeling action is exerted and the temperature of the skin surface is increased by the skin stimulation of the capsicum.

However, the conventional hot-type compress using the hot-type poultice containing the capsicum extract as a skin stimulating agent causes such inconveniences that a smarting pain feeling caused by the skin stimulating agent at the region applied to the affected part of the human body is too strong and later the applied region suffers from skin rashes, and so on. This cause is not unclear but it is presumed that capsaicin which is a component of the capsicum may be related thereto.

Then, any development of a hot-type compress which does not cause such inconveniences and can be safely used is desired.

DISCLOSURE OF THE INVENTION

The present invention is to provide a hot-type compress which removes the foregoing conventional inconveniences and meets,the foregoing desire, and which is characterized in that an applying face side composed of a sticky poultice plaster body formed on one side of a substrate sheet comprises an applying face composed of the sticky poultice plaster body and a uniformly distributed extract or powder of ginger.

One type of the above-mentioned hot-type compress is so constructed that a resultant one obtained by kneading a small amount of extract or powder of ginger with the sticky poultice plaster body as a main component is coated uniformly on one side of the substrate sheet to form a coat layer of the hot-type poultice plaster body.

Further, another type of the above-mentioned hot-type compress according to the present invention is so constructed that powder of ginger is coated uniformly on one side of the substrate sheet to form a ginger powder layer and the sticky poultice plaster body is partially coated on the surface thereof through a porous sheet Furthermore, further another preferable type of the hot-type compress according to the present invention is to provide a heat and hot-type compress which serves as a hot-type compress and also accelerates the warmth-feeling action and which is so constructed that a heat-emitting pad is provided integrally with the other side of the substrate sheet of each of the hot-type compresses comprising the foregoing types 1 and 2.

BEST MODE FOR CARRYING OUT OF THE INVENTION

Figure 1:
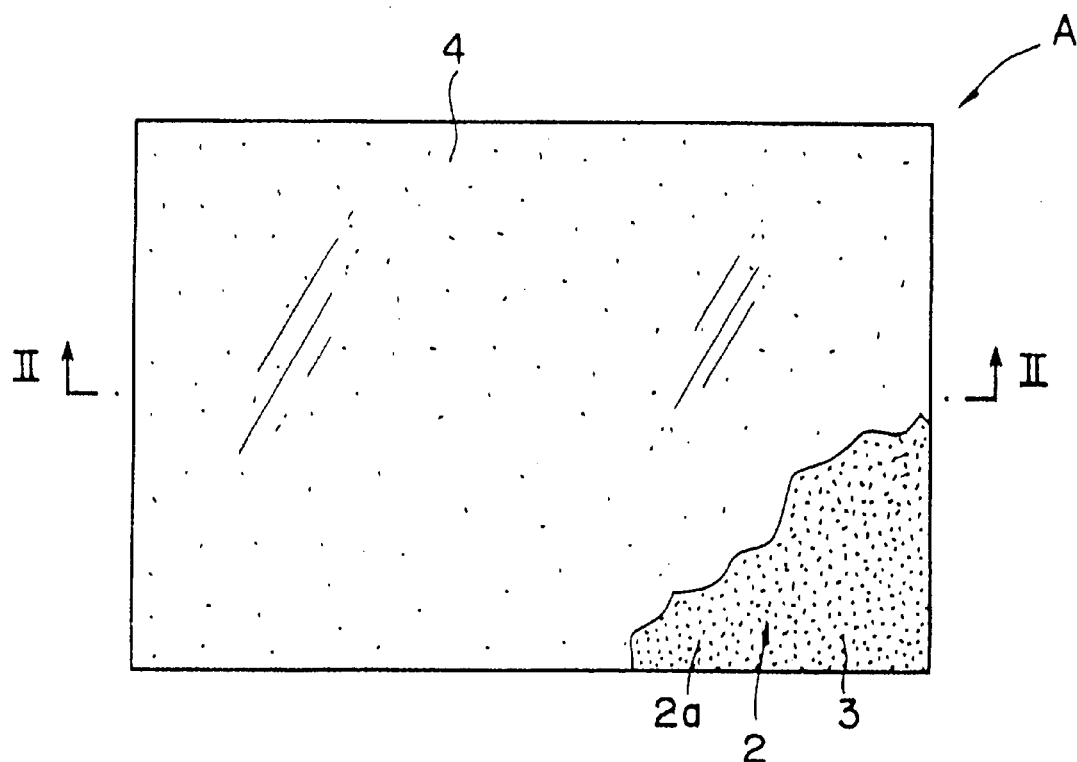
FIG. 1 is a partially omitted schematic plane view of one example of a hot-type compress according to the present invention.

A fundamental embodiment of a hot-type compress according to the present invention is a hot-type compress in which an applying face side composed of a sticky poultice plaster body formed on one side of a substrate sheet comprises an applying face composed of the sticky poultice plaster body and a uniformly distributed powder or extract of ginger.

The inventor of this application has searched for any substitute for capsicum hitherto used as a skin stimulating agent in the conventional hot-type compress, and as a result has found out that ginger exerts a warmth feeling stimulating action and a temperature rising action on the skin without having a bad effect on the skin. This cause is not clarified yet, but it has been found unexpectedly that such ingredients as zingerone, etc. which are known as pungent flavor ingredients contained in the ginger exert the warmth-feeling stimulating action and the temperature rising action on the skin, and in addition, these ingredients are not ones which cause such damage to the skin as rashes, scabs, etc. at the applied skin region as caused by the ingredients of capsicum, but ones which can be used safely and preferably. Ginger is prepared in the form of extract or powder. The powder is obtained, for instance, in such a manner that the raw material of ginger is washed, and thereafter is cut into pieces, and is dried by a solar drying, a heating drying, etc. and thereafter is pulverized or grounded by a pulverizer or grinder, or the like. Regarding the powder of ginger, an average particle size thereof in the range of about 40~300 meshes is generally used, but is not limited to this. And the extract thereof is obtained, for instance, in such manner that the raw material of ginger is cut into pieces, and the small pieces, as they are, or dried ones are extracted with an organic solvent as alcohol, ether, etc., or extracted with a supercritically pressured carbon dioxide. For more in detail, in the case of extraction with the organic solvents, an extract with a high concentration is obtained by dipping the foregoing small pieces in a 95% ethanol. In addition, in order to obtain a 100% extract from the raw material of ginger, it is attained by the supercritical pressure of carbon dioxide process. Namely, the raw material of ginger is washed and is cut into pieces and the small pieces are contained in a hermetically-sealed container and carbon dioxide gas is blown thereinto, and the extraction is carried out under the supercritical pressure thereof, and there is obtained the 100% ginger extract.

And, the hot-type compress according to the present invention as mentioned above is made usually into a product with a released paper sticked to the applying face thereof. When it is used, if the released paper is peeled off and is applied at the applying face thereof to the necessary part of a patient, and if any desired medicine, for instance, antiphlogistic and analgesic as an additive are added in the poultice plaster body, antiphlogistic and analgesic actions are exerted and at the same time, the warmth-feeling action and the temperature rising action are exerted on the skin, so that the blood flow is improved by the ginger contained according to the present invention.

Next, the modes for the embodiments according to the present invention will be explained detail with reference to the accompanying drawings.

Figure 2:
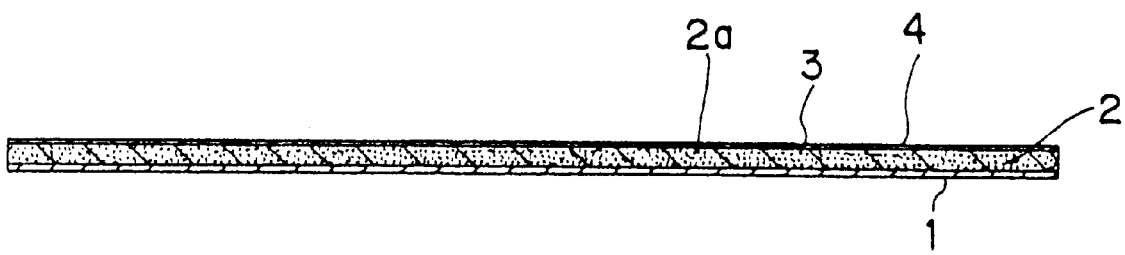
FIG. 2 is a sectional schematic view taken along the line II—II in FIG. 1.

FIG. 1 and FIG. 2 show a hot-type compress A according to one embodiment of the the present invention, and FIG. 1 is a plane view and FIG. 2 is a sectional view taken along the line II—II in FIG. 1. In the drawings, 1 denotes a substrate sheet made of polyester nonwoven fabric, etc., and 2 denotes such a coat layer of a hot-type sticky poultice plaster body according to the present invention that is formed in such a manner that a hot-type poultice plaster body according to the present invention prepared by adding 1~10 wt. % of the 100% ginger extract 3 obtained by the above-mentioned supercritical pressure carbon dioxide gas process to a sticky poultice plaster body 2a as a principal component, and kneading them together is coated uniformly on the whole surface of one side of the substrate sheet 1 by a hot melt coating process. Thus, there is obtained a product in which fine particle of the ginger extract 3 are contained in the sticky poultice plaster layer 2 and the innumerable particles of extract are distributed uniformly on the applying face of the coat layer 2. 4 denotes a released paper temporarily applied to the applying face of the surface of the coat layer 2. As the released paper 4 shown in the drawing, a transparent one such as of cellophane or the like is used, but an opaque one may be used. Thus, the hot-type compress A according to the present invention is constructed. Regarding the sticky poultice plaster body, various kinds of ones conventionally known may be used as desired.

The sticky poultice plaster body 2a, as a preferable example, comprises a thermoplastic polymer, which is capable of hot melt coating to the substrate, sheet, a tackifier agent , oil and filler. The polymer serves to provide the internal strength, i.e. a cohesive force of the hot-melt adhesive agent and prevent the sticky poultice from generation of the cold flow. Regarding the polymer, for instance, polystyrene resins, preferably, a block rubber comprising one kind or two of block-copolymers such as SIS, SBS, SEBS, SEPS, etc., is used. Especially, the block copolymer of SIS alone is used preferably.

Regarding the tackifier agent, rosin, rosin derivatives, terpene resins, petroleum resins with or without hydrogenation, or any other various kinds of hot melt adhesives are used. By blending this with foregoing polymer, it serves to offer the stickiness and wettability. Especially, in the relation of its compatiblity with the foregoing block rubber, terpene resins with or without hydrogenaton prepared by using a distilled $C_5$ fraction or a distilled $C_9$ fraction of the petroleum as a raw material is used preferably.

Regarding oils, for instance, a single of paraffin oil or naphthene oil is used, or both of them are used. When this is added to the foregoing blend, the viscosity of the blend can be decreased and thereby it serves to facilitate the hot melt coating thereof on the substrate sheet The paraffin oil is especially excellent in terms of the tone of color, stability to heat, and odor. Since the naphthene oil is good in compatibility, it has such a characteristics that the bleeding is made difficult.

Regarding the fillers, such white powders as zinc oxide, calcium carbonate, kaolin, and titanium oxide, etc. are used, and contribute to a die cutting property of a product, and further serve to make the poultice plaster body white and absorb the sweat or secrete during use thereof. The titanium oxide is more stable than other fillers and is higher in whiteness, and forms less scabs on the skin.

A small amount of an antioxidant or of one kind or more than two kinds of such medicines as antiphlogistic, analgesic of salicylic acid, or the like, when necessary, may be added in the poultice plaster body, or further a small amount of additives such as a moisture retaining agent such as glycerol, etc. a form-keeping agent such as polyacrylate, antioxidant, etc. may be added therein.

A preferably compounding composition of the sticky poultice plaster body is, for instance, as follows. Namely, it is composed of 17~40 parts by weight, preferably 20~35 parts by weight of SIS (styrene-iso-prene-styrene copolymer), 20~50 parts by weight of hydrogenated petroleum resin, 20~50 parts by weight of paraffin oil, and 1~5 parts by weight of titanium oxide. Further, it is preferable that 0.05~0.2 part by weight of a phenolic antoxidant as an additive is added. Furthermore, a small amount of any desired medicines or additives may be added to the above-mentioned sticky poultice plaster body. For instance, 0.7~3 parts by weight of antiphlogistic and analgesic and 0.1~1.0 part by weight of the moisture retaining agent may be added.

According to the present invention, for instance, a light yellow-colored hot-type sticky poultice plaster body can be prepared by adding 1~10 wt. % of the 100% ginger extract based on the sticky poultice plaster body, and kneading: them together. The example as shown in FIG. 1 is a product prepared by using this hot-type sticky poultice plaster body 2.

The hot-type compress A according to the present invention thus obtained, when it is used, if the released paper 4 is peeled off and is used by being applied to the affected part of a patient, the warmth is felt and the temperature is raised at the applied region, so that the blood flow is accelerated by the ginger extract 3 uniformly distributed on the applying face thereof.

There has been observed in the hot-type sticky poultice plaster body 2 of the foregoing hot-type compress A which is the above-mentioned one example of the present invention such a phenomenon that it initially assumes a light yellow, but with a long lapse of time after the application thereof, it changes into white. As a result of examination thereof, it has been confirmed that the ginger extract is evaporated and vanished at that time. Accordingly, such a convenience in the application thereof that a user be able to judge the effective time of the applied hot-type compress A by looking at the change of the color thereof can be given to the user.

Furthermore, though not illustrated, such a product may be prepared by kneading, instead of ginger extract ginger powder with the foregoing sticky poultice plaster body to make a hot-type one and coating the hot-type one and forming on the substrate sheet In this case, it is in general and preferable that an addition amount of the ginger powder is in the range of 10~50 wt. % based on the sticky poultice plaster body. Especially, at the time of kneading thereof, when the powder comprising fine particles in the range of 250~300 meshes as the particle size of the powder is used, a hot-type sticky poultice plaster body in which the powder is easily mixed uniformly by kneading is obtained.

Figure 3:
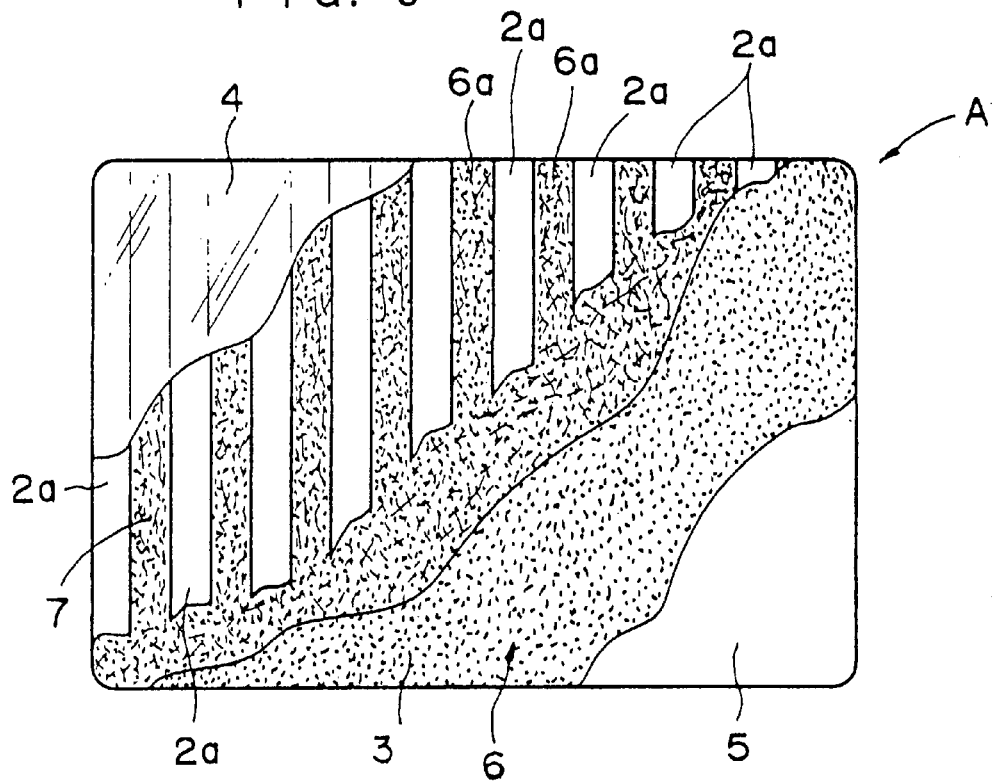
FIG. 3 is a partially omitted schematic plane view of another example of a hot-type compress according to the present invention.
Figure 4:
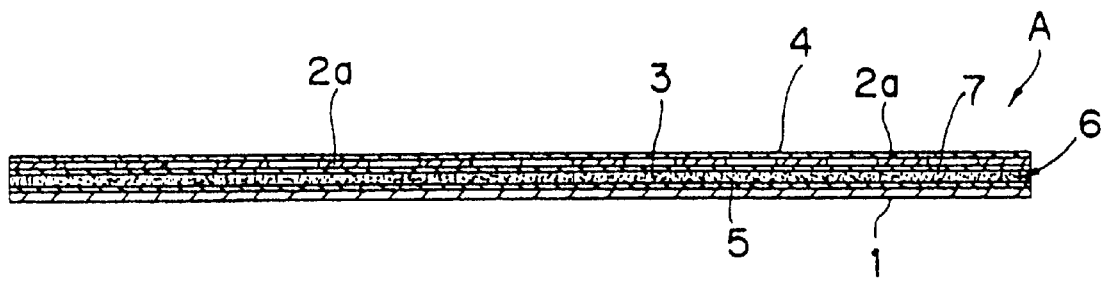
FIG. 4 is a sectional schematic view taken along the line IV—IV in FIG. 3.

FIG. 3 and FIG. 4 show another mode of the embodying example of the present invention. In this mode of the embodying example, the ginger powder is used, and is positioned on the applying side and over a comparatively large area so as to face the skin surface, so that the use efficiency thereof is increased.

Namely, in this example, a 2nd type of the hot-type compress according to the present invention is so constructed that a sticky agent or an adhesive agent of an acryl type or rubber type is coated uniformly on a whole surface of one side of the substrate sheet 1, and the ginger powder 3 of which an average particle size is generally in the range of 40~300 meshes is adhered through the resultant coat layer 5 uniformly to the whole surface thereof in the range of 3 g~20 g/m$^2$ in density, so that an adhered layer of the ginger powder is formed, and a porous sheet 7 which is made of woven fabric or nonwoven fabric and which does not pass the ginger powder, but passes the sticky agent is put thereupon, and a conventional hot-type poultice plaster body in which antiphlogistic and analgesic are added and mixed is coated partially on the upper surface of the porous sheet 7 by the hot-melt coating process, so that a coat layer 2a thereof is formed, and a released paper 4 is temporarily applied to the outer surface thereof.

The partial coating of the sticky poultice plaster body 2a is carried out by coating thereof in the form of dots or lines, but in the illustrated example, a stripe having a predetermined small width is coated partially with regular spaces to be formed in a regular striped pattern comprising a large number of the stripes. Thus, there is constructed a product in which a pattern of regular yellow-colored stripes 6a, 6a, . . . of the ginger powder layer 6 are observed between the respective adjacent ones of these white coat layers 2a, 2a, . . . of the striped pattern through the porous sheet 7. The thickness of the coat layer 2a of the sticky poultice is, for instance, preferably, 60–200 μm.

And, these sticky poultice plaster bodies 2a partially coated, at the time of coating, penetrates through the innumerable meshes of the porous sheet 7 into the underlying ginger powder layer 6 and further to the underlying adhesive layer 5, so that the porous sheet 7 is fixed to the upper surface of the ginger powder layer 6, and thereby it is arranged that the powder particles of the ginger powder layer 6 may be prevented from falling to the outside and a predetermined amount of the good ginger powder layer 6 may be held safely.

This hot-type compress A, when it is used, the released paper 4 is peeled, and it is applied to the affected part with its partially applying face comprising the coat layers 2a, 2a, . . . of the striped sticky poultice plaster body. Whereupon, the antiphlogistic and analgesic actions exert on the applied region by the poultice plaster body, and at the same time a large number of lines of the striped parts 6a, 6a, . . . of the ginger powder layer 6 face the affected part and exert the warmth-feeling stipulation and the temperature rising action thereon, so that improvement in the blood flow is brought about In this case, owing to the interposition of the porous sheet 7, excess skin stimulation caused by the direct contact of the ginger powder with the skin can be relieved especially for a patient whose skin is week.

Further, though not illustrated, a 2nd type of hot-type compress may be so constructed that instead of the ginger powder, ginger extract is coated through the coat layer 5 of the sticky agent or adhesive agent on the substrate sheet to form a coat film thereof, and the porous sheet 7 is applied to the upper surface thereof, and the sticky poultice plaster body is applied partially in the shape of dots or lines.

Furthermore, according to the present invention, as an alternative example thereof, a heat and hot-type compress which can exert simultaneously a heating action and the warmth-feeling action by providing a heating pad integrally with the foregoing hot-type compress may be constructed.

Figure 5:
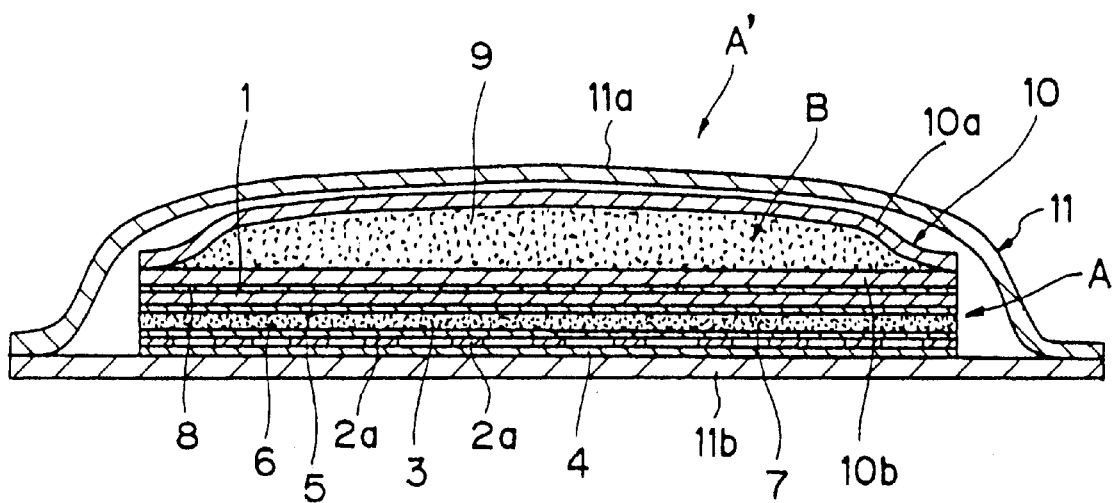
FIG. 5 is a partially omitted schematic sectional view of a further another example of a heat and hot-type compress according to the present invention.

One example thereof is shown in FIG. 5. It is such a one that a heat-emitting pad B is provided integrally with the 2nd type of hot-type compress according to the present invention.

In the same Figures, since A is a hot-type compress which is the same construction as the above mentioned example, the respective components are indicated by the same symbols as mentioned above. However, it is necessary for the substrate sheet 1 to be made of a gas permeable nonwoven fabric or woven fabric. A flat heat-emitting pad B is applied through an adhesive agent or adhesive agent 8 thinly applied with a sticky agent or an adhesive agent partially or wholly to the whole surface of the outer surface, that is, the other side of the substrate sheet 1 of the hot-type compress A The warmth-emitting pad B is constructed by containing a heat-emitting body 9 in a gas a permeable bag 10 which is flat in shape and has a suitable gas permeability. The gas permeable bag 10 is the two upper and lower sheets 10a and 10b in the drawings, and the peripheral edge parts thereof are bonded together by heat-sealing. The upper sheet 10a comprises a lamination sheet which is gas permeable as a whole, which has a suitable gas permeability as a whole: and which is prepared by putting a low density polyethylene film positioned inside and a polyester film positioned outside one upon another and binding them together. The lower sheet 10b comprises a lamination sheet which has a suitable gas permeability as a whole, and is prepared by binding a low-density polyethylene film positioned inside and a polyester film positioned outside together.

The heat-emitting body 9 is a powdery mixture which is composed mainly of iron powder and which is prepared by being added and mixed with respective proper amounts of moisture retaining and pore-keeping agents composed generally of common salt, activated carbon, powdery wood, vermiculite, or the like. The composition of this heat-emitting body 9 is, for instance, composed of 56 wt. % of reduced iron powder or cast iron powder, 12.4 wt. % of water, 17.2 wt. % of activated carbon, 10.8 wt. % of vermiculite or powdery wood, and 3.6 wt. % of salts.

Thus, there is obtained a heat and hot type compress A' according to the present invention in which the 2nd type of hot-type compress A and the heat-emitting pad B are constructed integrally one with another. However, if it remains as it is, the external air penetrates through the gas permeable bag 10 of the heat-emitting pad B into the inside thereof, and reacts with the heat-emitting body 9 to emit the heat, and therefore the heat and hot-type compress A' is contained in a packing bag 11 which is nonpermeable to gas and is hermetically sealed to be made into an air-tight product The gas non-permeable packing bag 11 is formed by heat-sealing the peripheral edge parts of an upper sheet 11a and the peripheral edge parts of a lower sheet 11b. Each of the respective sheets 11a, 11b comprises a lamination sheet comprising a low-density polyethylene film positioned inside and an elongated polypropylene film positioned outside and a polyvinylidene chloride film interposed therebetween.

The above-mentioned heat and hot-type compress A', at the time of use thereof, is taken out to the outside by breaking the packing bag 11, and the released paper 4 is peeled off, and It is applied to the required part of a human body with the applying face having the striped sticky poultice plaster bodies 2a, 2a, . . . Whereupon, the ginger powder layer 6, at its striped exposure parts 6a, 6a, . . . faces, through the porous sheet 7, the skin, so that the warmth-feeling action is exerted thereon while the skin stimulation is being relieved.

On the other hand, under this use condition, at the same time, since the heat-emitting body 9 in the heat-emitting pad B is supplied property with the external gas (air) through the gas permeable sheet 8a of the gas permeable bag 10, the temperature is raised by the exothermic reaction, and the proper temperature of about 37~43° C. is continued, and the affected part is heated, so that it exhibits such heat effects that the blood flow is improved, the fatigue of the muscles is removed, the stillness of the muscles is relaxed, the pain is relieved, the fatigue thereof is recovered, etc. Accordingly, the deep warmth-feeling is given to the affected part in conjunction with the above-mentioned heating action. In this case, since the ginger powder itself also is heated to such high temperatures as 37~43° C., the warmth-feeling action is accelerated. Further, regarding the sticky poultice plaster body, for instance, there may be used a poultice plaster body comprising a thickener such as sodium alginate, methyl cellulose, polyvinyl alcohol or the like, the moisture retaining agent comprising a polyhydric alcohol such as glycerin, etc., a filler comprising an inorganic material such as kaolin, etc., a viscosity-adjusting agent such as polybutene, etc., and a cross-linking agent such as acetaldehyde, aluminum chloride, etc.

The ginger powder layer 6 used in the example of the above-mentioned heat and hot-type compress A' may be changed by the coat layer of the ginger extract. And, in this case, in stead of the above-mentioned heat and hot-type compress A', a heat and hot-type may be constructed by using the 1st type of the hot-type compress A which is provided with the heat-emitting pad B bonded to the upper surface thereof as mentioned above.

Thus, according to the present invention, since a hot-type compress is so constructed that a compress of which one side thereof has an applying face of a sticky poultice plaster body is provided with extract or powder of ginger uniformly distributed on the applying face, when it is applied to the affected part, not only the warmth-feeling action is exerted on the applied region, but also the scabs that would be formed in the case of the capsicum extract are not formed on the applied region, and thus a safe and good hot-type compress can be provided. Further, when a hot-type compress is so constructed that a porous sheet is put on the outer surface of a ginger powder layer on one side of the substrate sheet, and the sticky poultice plaster body is partially coated on the outer surface thereof, the skin stimulation can be relieved, and in the case of the powder layer, falling of the ginger powder therefrom can be prevented, so that a stable and good product which withstands the vibrations and shocks can be obtained. Furthermore, when a heat and hot-type compress is constructed by providing a heat-emitting pad integrally with the foregoing hot-type compress, the heat action and the deep warmth-feeling under this heat are exerted simultaneously on the applied region.

INDUSTRIAL APPLICABILITY

Thus, the hot-type compress according to the present invention can be produced on a mass production basis and is applicable as a health keeping for a human body and as a medical appliance.

I claim:

1. A heat and warmth- feeling stimulation compress comprising a warmth-feeling stimulation compress which comprises:
    a) a substrate sheet with an application face side and a heat emitting side, wherein the application face side comprises a sticky poultice plaster body, and the heat emitting side comprises a heat emitting gas-permeable pad,
    b) wherein the sticky poultice plaster body further comprises a uniformly distributed layer of extract or powder of ginger and a porous sheet applied to the layer of ginger so the sticky poultice plaster body is coated partially through the porous sheet, and
    c) wherein the heat emitting pad further comprises a heat emitting body comprising iron.

2. A heat and warmth feeling stimulation compress according to claim 1, wherein the heat-emitting body contained with the heat emitting gas-permeable pad comprises iron powder with salts, activated carbon, vermiculite, and water.

* * * * *